United States Patent

Tiller et al.

[11] Patent Number: 5,948,474
[45] Date of Patent: *Sep. 7, 1999

[54] BIO-ACTIVE ROCK AND METHOD FOR MAKING THE SAME

[76] Inventors: Norman Andrew Tiller, 452 Kinghorn Dr., Nampa, Id. 83651; Louis George Grundel, 801 I St., Rupert, Id. 83350

[*] Notice: This patent is subject to a terminal disclaimer.

[21] Appl. No.: 08/824,018

[22] Filed: Mar. 21, 1997

Related U.S. Application Data

[63] Continuation-in-part of application No. 08/546,479, Oct. 20, 1995, Pat. No. 5,702,780.

[51] Int. Cl.$^6$ ............................................. B44C 3/06
[52] U.S. Cl. ............................ 427/294; 428/15; 428/540; 428/907
[58] Field of Search ............................ 428/15, 905, 907, 428/540; 427/294

[56] References Cited

U.S. PATENT DOCUMENTS

| | | | |
|---|---|---|---|
| 3,547,688 | 12/1970 | Gagliardi et al. | 428/907 X |
| 3,551,192 | 12/1970 | Reinert | 428/907 X |
| 4,115,130 | 9/1978 | Crump et al. | 428/907 X |
| 4,169,088 | 9/1979 | Hansen | 428/907 X |
| 4,258,090 | 3/1981 | Moraru | 428/907 X |
| 4,880,690 | 11/1989 | Szycher et al. | 428/905 X |
| 5,702,780 | 12/1997 | Tiller et al. | 428/15 |

*Primary Examiner*—Henry F. Epstein
*Attorney, Agent, or Firm*—Robert L. Shaver; Frank J. Dykas

[57] ABSTRACT

A method for impregnating rock or landscaping material with bio-active and/or colored fluid. To impregnate the rock or landscaping material with bio-active chemical, the rock or landscaping material is heated to dehydrate it, and cooled to an ambient temperature in a dehumidified chamber, and then placed in a pressurizable container which is filled with bio-active chemical. The pressurizable container is placed under pressure for a sufficient time that the bio-active fluid is forced into the interstices of the rock or landscaping material. When the rock or landscaping material is removed from the pressurizable container, it has been impregnated with bio-active chemical and gradually emits the bio-active chemical. The rock or landscaping material may be cleaned using water or a solvent. The bio-active chemical used can be a herbicide, pesticide, plant or insect growth hormones, repellents of cats, dogs, mice, or other pests, or fertilizers.

13 Claims, 3 Drawing Sheets

BIO-ACTIVE ROCK AND METHOD FOR MAKING THE SAME

This application is a continuation-in-part of application Ser. No. 08/546,479 filed Oct. 20, 1995 and now U.S. Pat. No. 5,702,780.

BACKGROUND OF THE INVENTION

1. Technical Field

This invention generally relates to bio active rocks and a method of making bio-active rocks, and more particularly to a process for impregnating rock with a bio-active chemical.

2. Background

Crushed rocks, porous lava rocks, gravel, pea gravel, river stone, flagstone, bricks, crushed bricks, ceramics, porcelain, wood strips and plastic strips are commonly used as landscaping materials around a building. These materials can be used as ground cover around bushes, to form walk ways, to form the border between areas of lawn and shrubbery, and to provide mulch around plants.

There are many chemicals which are commonly applied in the same areas where these landscaping materials are utilized. These chemicals can include herbicides to prevent the growth of grass in non-grassy areas, herbicides to prevent the growth of anything in certain areas, pesticides to kill insect populations, growth regulators to prevent germination or maturation, animal repellents to discourage cats, dogs, mice, etc., or fertilizers to release nutrients into the soil around plants. These chemicals can be applied in a variety of methods, including dripped through trickle irrigation systems, sprayed on the plants and the ground, deposited as granules on the ground with a time release capability, or inserted into the soil in chemical releasing stakes.

What is needed is a product which utilizes conventional materials of landscaping, such as rocks, lava stones, gravel, brick, ceramic, as a carrying agent and release site for bio active chemicals, such as pesticides, herbicides, growth hormones, repellents and fertilizers.

Accordingly, it is an object of this invention to provide landscaping materials made from rocks, lava stones, pea gravel, brick, crushed brick, flag stones, vermiculite, ceramic, porcelain, which can be utilized in landscaping environments and which are impregnated with, and which gradually release pesticides, herbicides, growth hormones, repellents or fertilizers selected by the user.

A further object of the present invention is to provide a method of impregnating the landscaping materials with a bio-active agent, such as pesticides, herbicides, fertilizers, repellents, or growth hormones.

DISCLOSURE OF INVENTION

These objects are accomplished by heating the rock or landscaping material for a sufficient time and at a sufficient temperature and pressure to drive away moisture. For opal, the temperature and pressure of 220° F. and no vacuum has proven effective. Other rocks or minerals would require different settings, including a negative pressure for which a vacuum oven would be utilized. The rock or landscaping material is then placed in a pressurizable container into which a bio-active chemical fluid is also placed. The pressurizable container is placed under pressure, which forces the bio-active fluid into the interstices of the rock or landscaping material which had previously been occupied by water. After suitable time and pressure to impregnate the pores of the rock or the mineral with the bio-active fluid, (for opal this can be 24 hours and 1000–1500 p.s.i.) the pressure is released and the stone is removed. The rock or landscaping material is then cleaned with water or a solvent. The rock or landscaping material will then emit a bio active chemical and will continue to do so for a very long period of time. Alternatively, some materials can be impregnated under atmospheric pressure.

BEST MODE OF THE INVENTION

Referring to FIGS. 1 through 5, the method of impregnating a rock with a bio-active chemical is shown in schematic representation format. This invention can also be utilized in other applications involving the growing of plants or landscaping situations. This can include ceramic figurines, which are kept indoors but which may hold plants or serve as an indoor water fountain. The method could also be used for impregnating flower pots with bio-active agents, such as growth hormones or fertilizers. The method can also be used for impregnating bricks or cinder blocks with bio-active agents, such as a pesticide, herbicide, or repellent. The method can be utilized to impregnate nursery items with bio-active agents. These nursery items can include clay pots, or other materials which can absorb a chemical. Although the invention principally relates to rocks, other landscaping materials are equally suited to this process. Under the term "rocks" are included pea gravel made from any type of rock, lava stones, such as crushed pumice, lava stone in the form of boulders, landscaping rock in the form of boulders, bricks, crushed bricks, slate, flag stones, cobble stones, river stones, cinder blocks, crushed rock, plastic edging strips, or other landscaping materials. It is a process by which a hydrated or porous rock or landscaping material is impregnated with a bio-active fluid. Hydrated rocks are defined as any rock that has water bound up in it, either chemically bound or contained within the rock matrix as a liquid or as a mono-layer.

By heating the rock to drive off the unbound and loosely bound water contained within the porosities of the rock, and then replacing that water with fluid which contains a bio-active chemical, the porosities of the rock, which can be from 0 to 45%, become a reservoir of bio-active fluid. The bio-active chemical from the fluid is gradually released through the porosities of the rock and is also bound to the surface of the rock.

In the preferred embodiment of the Applicant's invention, the rocks or landscaping material are heated in a dehumidified container, at least to the boiling point of water, in order to drive off any water that may be held within. Using opal as an example, a temperature of 220° F. has proven adequate for dehydration. Again, using opal as an example, 24 hours has been sufficient time to dehydrate the opal. A vacuum oven can be used to speed the removal of water and to more thoroughly remove water. After heating, the rocks or minerals are cooled to ambient temperature in a chamber which is dehumidified using a desiccant.

Figure 1:
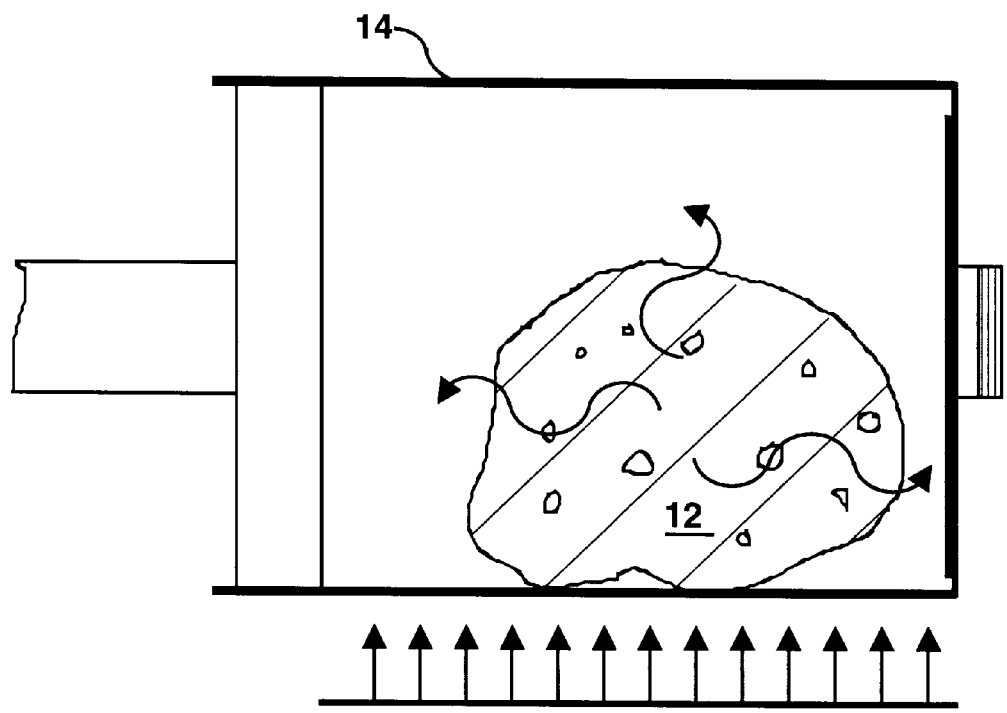
FIG. 1 is a schematic representation of a hydrated rock in a chamber to which heat is applied and water vapor from the rock is driven off.
Figure 2:
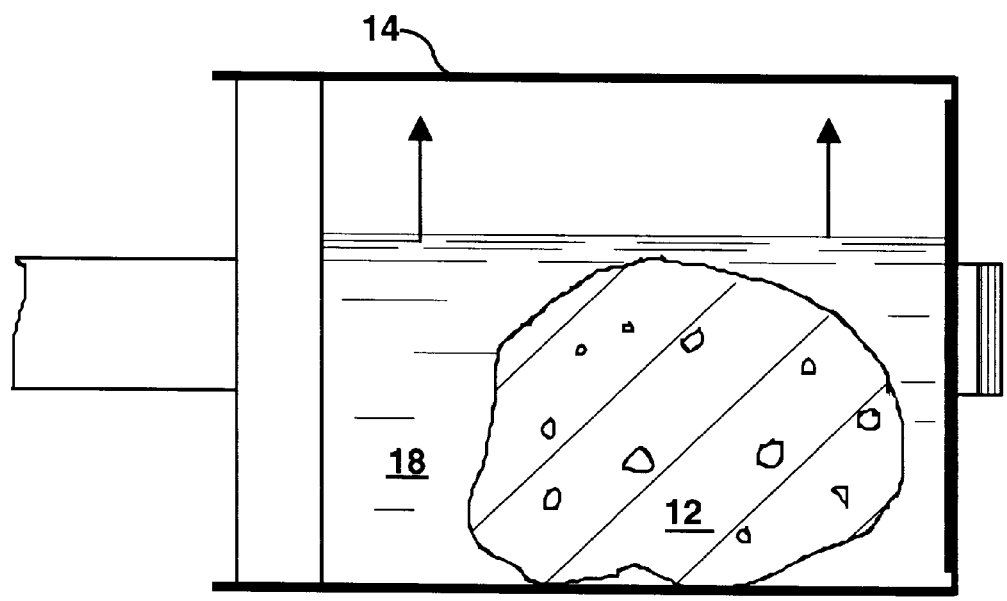
FIG. 2 is a schematic representation of the dehydrated rock immersed in a bio-active fluid in a pressurizable container.
Figure 3:
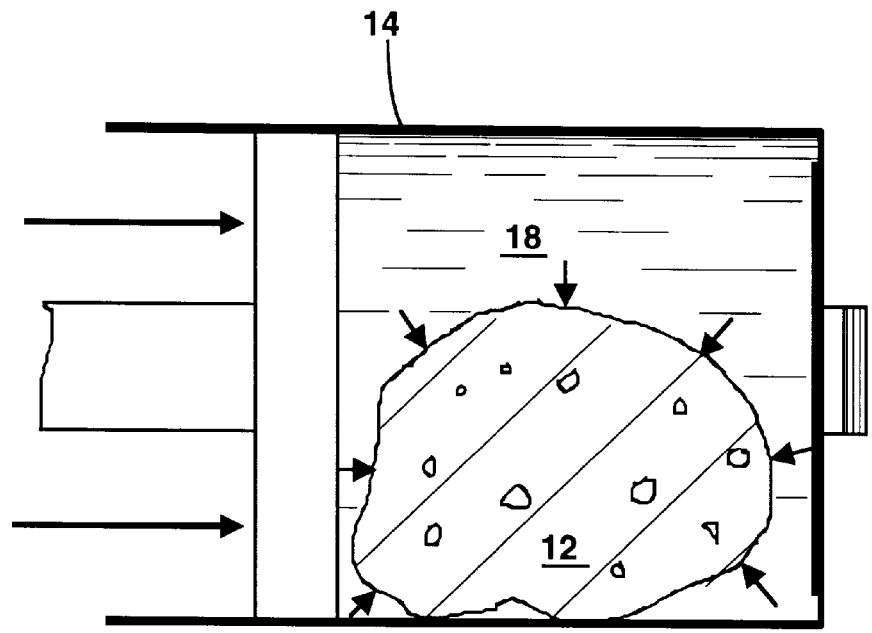
FIG. 3 is a schematic representation of the dehydrated rock immersed in bio-active fluid in a pressurizable container to which pressure is being applied.
Figure 4:
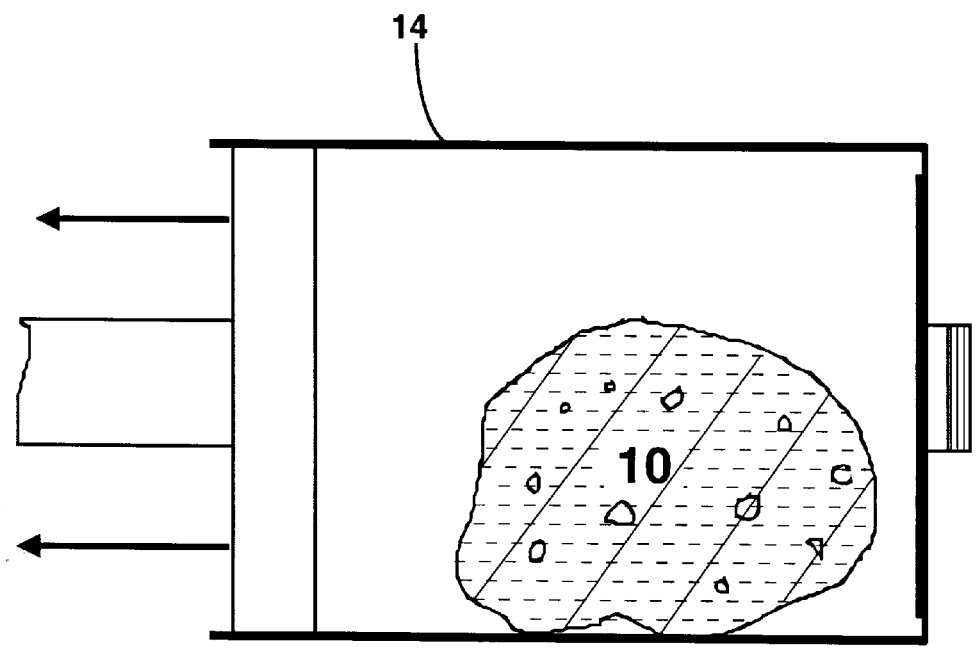
FIG. 4 is a schematic representation of a rock impregnated with a bio-active fluid.
Figure 5:
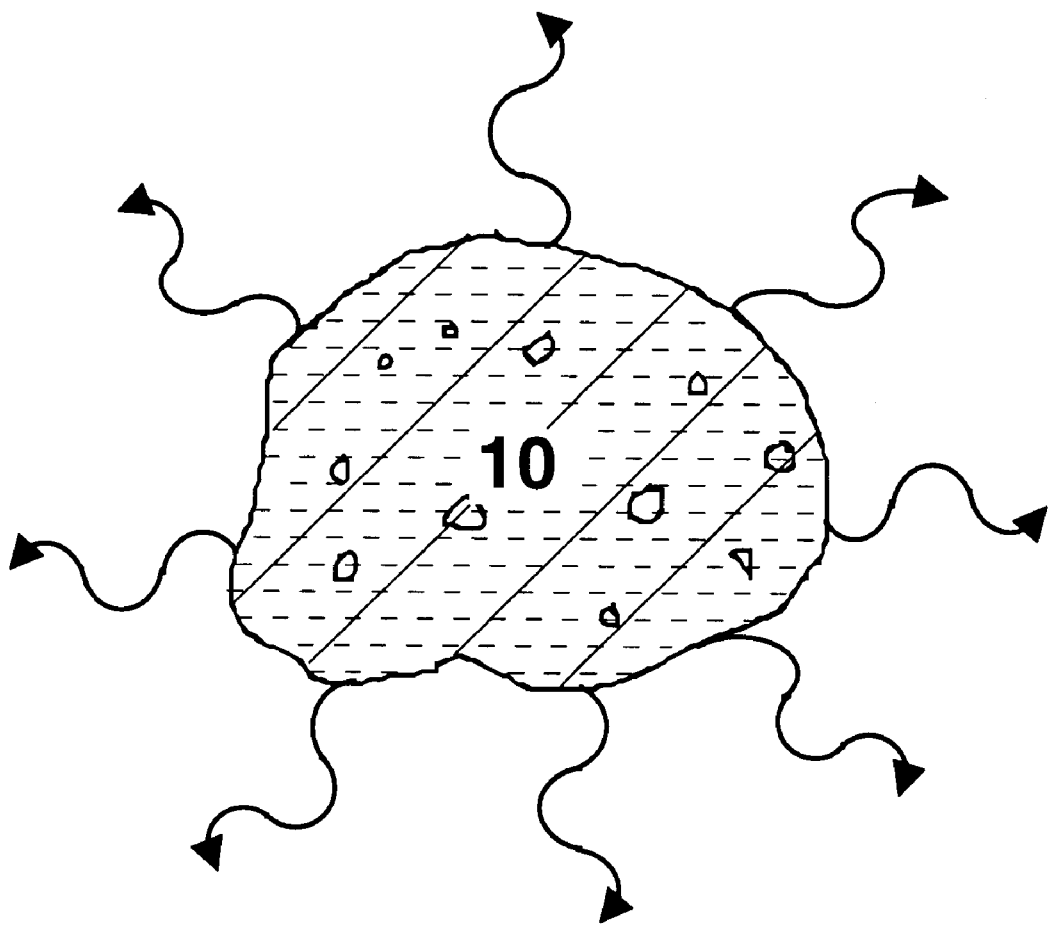
FIG. 5 shows the rock or landscaping material which has been impregnated with bio-active fluid in it's final form.

The now dehydrated rock or landscaping material is placed in a pressurizable container (14) which is filled with a bio-active fluid (18). The pressurizable container is placed under pressure as shown in FIG. 3 for a preselected time and a preselected pressure to force the bio-active fluid into the porosities of the dehydrated rock or landscaping material. Using opal as an example, a pressure of 1000–1500 p.s.i. has proven suitable. After a period of time under the required pressure, the pressure is released and the remaining fluid is removed. Using opal as an example, 24 hours has proven to be a sufficient time. Using jasper, 48 hours has been required.

After the rock or landscaping material is removed from the vacuum chamber, it may be cleaned using water or a solvent.

While this is the preferred embodiment of the process, the process can take other forms as well. The container in which the rock or landscaping material is heated for dehydration can be a vacuum oven. It can also be a container made of sintered metal. The bio-active fluid which is impregnated under pressure into the rock or landscaping material matrix can be an aqueous, or water based fluid. It can also be an organic, or oil based fluid. The bio-active fluid which is impregnated into the rock can also contain a dye which colors the rock. This color would be utilized as part of the characteristic of the landscape material. Some materials can be impregnated with bio-active chemicals without applying pressure, but by merely soaking the materials in the bio-active chemicals under atmospheric pressure.

The rock or landscaping material (10), which now has been impregnated with the bio-active fluid, is removed from the pressurizable container. When the process is complete the rock or landscaping material will have several desirable attributes. It will emit bio-active chemicals which can be utilized to advantage in landscaping. These can be pesticides, herbicides, fertilizers, animal repellents, or growth hormones. The rock or landscaping material with the chosen bio-active chemicals can be spread throughout the landscaping and utilized to prevent the growth of weeds in unwanted areas, prevent the growth of any plants in certain areas, or control populations of insects, to repel cats, dogs, mice or other pests, or to introduce fertilizers into the area where they are spread.

Since the bio-active rock or landscaping material can be made from a wide variety of porous or hydrated minerals, the final product will also have the attribute of color and texture which can be used in combination with being bio-active.

In use, the bio-active rock or landscaping material can be used as ground cover, to form garden walkways, to spread around the base of buildings as part of landscaping, to use as ground cover around shrubbery, and to replace the rocks, bark, bricks, or other landscaping material which is utilized throughout the landscaped area. Since the bio-active material would gradually be emitted from the rock or landscaping material, its rate of emission would be determined by the porosity of the rock, the volatility of the bio-active chemical, the pore size of the rock, and the affinity of the surface of the rock for a bio-active chemical. Rocks or landscaping materials could be chosen for the desired emission rate of the bio-active chemical.

While there is shown and described the present preferred embodiment of the invention, it is to be distinctly understood that this invention is not limited thereto but may be variously embodied to practice within the scope of the following claims.

We claim:

1. A method of impregnating a hydrated or porous rock or landscaping material with a bio-active chemical, which comprises:

(a) dehydrating the rock or landscaping material using heat;

(b) cooling the rock or landscaping material to an ambient temperature in a dehumidified chamber;

(c) placing the rock or landscaping material in a pressurizable container;

(d) filling the pressurizable container with a bio-active chemical;

(e) pressurizing the container for a preselected period of time, and at a preselected pressure to impregnate the rock or landscaping material with the bio-active chemical;

(f) depressurizing the container;

(g) removing the bio-active rock or landscaping material from the pressurizable container.

2. The method of claim 1, wherein the rock or landscaping material is impregnated with one or more bio-active chemicals under atmospheric pressure.

3. The method of claim 1, wherein the rock or landscaping material is cleaned with a solvent after being removed from the pressurizable container.

4. The method of claim 3, wherein the solvent used to clean the rock consists of an alcohol.

5. The method of claim 1, wherein the rock or landscaping material is dehydrated in a vacuum oven.

6. The method of claim 5, wherein the dehydration step takes place in a sintered container.

7. The method of claim 1, wherein the rock or landscaping material is heated to approximately 220° F. to dehydrate the rock or landscaping material.

8. The method of claim 1 wherein the bio-active chemical comprises of an aqueous solution plus a bio-active chemical.

9. The method of claim 1, wherein the bio-active chemical consists of an organic solution of an oil and a bio-active chemical.

10. The method of claim 1, wherein the bio-active chemical is also colored.

11. The method of claim 1, wherein a hydraulic cylinder is used to pressurize the bio-active chemical and rock or landscaping material.

12. The method of claim 11, wherein the container is pressurized to within the range of 1500 to 3000 psi.

13. A method of impregnating a hydrated or porous rock or landscaping material, with a bio-active chemical which comprises:

(a) placing a rock or landscaping material in a container;

(b) dehydrating the rock or landscaping material;

(c) filling the container with a bio-active chemical;

(d) pressurizing the container for a preselected time and at a preselected pressure to impregnate the rock or landscaping material with a bio-active chemical;

(e) depressurizing the container;

(f) removing the rock or landscaping material from the container.

* * * * *